United States Patent [19]
Carnazzo

[11] Patent Number: 5,925,378
[45] Date of Patent: Jul. 20, 1999

[54] METHOD FOR ENHANCING DELIVERY AND UNIFORMITY OF CONCENTRATION OF CELLULAR CREATINE

[75] Inventor: Joseph W. Carnazzo, Boys Town, Nebr.

[73] Assignee: Fortress Systems, L.L.C., Omaha, Nebr.

[21] Appl. No.: 08/829,198

[22] Filed: Mar. 31, 1997

[51] Int. Cl.⁶ ..................................... A61K 9/46
[52] U.S. Cl. ........................... 424/466; 424/489; 424/464
[58] Field of Search .................................... 424/466, 489, 424/273, 48

[56] References Cited

U.S. PATENT DOCUMENTS 4,255,438  3/1981  Kane et al. ............................. 424/273
4,390,523  6/1983  Huchette et al. ......................... 424/48

*Primary Examiner*—Thurman K. Page
*Assistant Examiner*—William E. Benston, Jr.
*Attorney, Agent, or Firm*—Zarley,McKee,Thomte,Voorhees & Sease; James A. Napier

[57] ABSTRACT

A method for enhancing a stable concentration of cellular creatine in a human includes dissolving an effervescent containing an acidic edible salt form of creatine in water. Once the mixture has completely dissolved the solution is immediately ingested, and an effective amount of creatine is absorbed. Preferably, the effervescent is in the form of a tablet which contains creatine in the form of an edible salt, a mixture of acids, and sodium.

19 Claims, No Drawings

METHOD FOR ENHANCING DELIVERY AND UNIFORMITY OF CONCENTRATION OF CELLULAR CREATINE

TECHNICAL FIELD

The present invention relates generally to oral nutritional supplements, and more particularly to a method for enhancing a stable concentration of cellular creatine in a human.

BACKGROUND OF THE INVENTION

Creatine oral supplementation has been used in the prior art to increase creatine and creatine phosphate (also called phosphocreatine) stores, which are needed for high energy phosphorus metabolism. Creatine, along with dietary carbohydrates, fats, proteins, and other compounds, is a central component of the metabolic system, and is involved in the provision of energy for work and exercise performance. Phosphocreatine helps provide Adenosine TriPhosphate (ATP) during short bursts of high intensity exercise, and it has been found that the depletion of phosphocreatine has been associated with the onset of fatigue. It has been recently discovered that the phosphocreatine pool in skeletal muscle is expandable. This has led to the oral supplementation of creatine and phosphocreatine to increase the levels of these components in muscle, to thereby enhance exercise performance during intermittent activities which require strength and power.

Recovery after high intensity exercise involves a resynthesis of phosphocreatine, which occurs via an oxygen-dependent process with half-life of about 30 seconds. During short-term high intensity intermittent exercise, the active muscles rely heavily on phosphocreatine for production of ATP. The rate of phosphocreatine resynthesis can be accelerated by the use of creatine supplementation in subjects who demonstrated an increase in creatine concentration. The benefits of creatine supplementation are particularly evident in high intensity activities that are intermittent in nature.

Creatine is synthesized from amino acids in the liver, pancreas and kidney, by the transfer of the guanidine moiety of arginine to glycine, which is then methylated to form creatine. Creatine which is synthesized in the liver, pancreas and kidney, is released into the bloodstream and actively taken up by the muscle cells, using the Na+ gradient. Oral creatine is absorbed, unchanged, from the intestinal lumen and passes directly into the bloodstream. The cellular creatine concentration is determined by specific transporters, which transport creatine into the cell against its concentration gradient.

The creatine transport protein has an increased affinity for creatine and concentrates creatine within the cell. Once inside the cell, very little creatine is lost (approximately 2 grams per day in a 70 kg male). Based upon this information, it follows that small increases of plasma creatine (which can occur with creatine supplementation) result in increased transport activity. The loss of creatine from skeletal muscle is typically about 3% per day, which closely matches the amount of creatinine produced non-enzymatically by living human muscle. The main mechanism by which creatine is lost, is the conversion of creatine to creatinine, which is an irreversible non-enzymatic process. Thus, creatine lost from a cell is considered to be negligible, and the concentration of creatine in the cell is not at risk of depletion by virtue of exercise. Thus, the main advantage of creatine administration is in the fact that cellular creatine concentration is stable and not prone to being lost.

The most commonly used creatine supplement for oral consumption, is creatine monohydrate. Creatine monohydrate supplementation at a dosage of 20 grams per day for a 5 day period has been the standard used during most studies in humans. Conventionally, creatine monohydrate is dissolved in approximately 300 milliliters of warm to hot water, the increased water temperature thereby increasing the solubility of creatine monohydrate. It has been found that creatine is not decomposed in the alimentary tract after oral administration, since there is no appreciable increase in urinary urea or ammonia. The results obtained for the conversion of retained creatine to creatinine have led researchers to believe that creatine is completely absorbed from the alimentary tract, then carried to the tissues, and thence either stored in the tissues or immediately rejected and eliminated by way of the kidneys.

The main problem with existing creatine supplementation is in the ability to provide consistent uniform results. It is believed that these inconsistent results arise because of the current methods of delivering creatine to the human body area. Current creatine oral supplementation, as discussed above relies on the use of creatine in powder form which is dissolved in water and then taken orally. However, creatine in powder form does not dissolve well in water or other neutral pH liquids. While increasing the temperature of the water increases the solubility of creatine monohydrate, there still is no consistency in the amount of creatine which is effectively dissolved in the water. For this reason, the consumer will take in varying amounts of creatine when consuming the water.

SUMMARY OF THE INVENTION

It is therefore a general object of the present invention to provide a method for delivering precise unit dosages of creatine to the human body.

Another object of the present invention is to provide a method of delivering creatine in the form of an oral supplement in a more readily absorbable form than prior art powders.

Still another object is to provide a creatine oral supplement which is highly soluble, absorbable, and provides consistent, uniform, and accurate delivery of the creatine to the human cells.

These and other objects of the present invention will be apparent to those skilled in the art.

The method for enhancing a stable concentration of cellular creatine in a human includes dissolving an effervescent containing an acidic edible salt form of creatine in water. Once the tablet has completely dissolved the solution is ingested, and an effective amount of creatine is absorbed. Preferably, the effervescent is in tablet form and contains creatine in the form of an edible salt, a mixture of acids and sodium bicarbonate, which release carbon dioxide when dissolved in the water.

DESCRIPTION OF THE PREFERRED EMBODIMENT

The inventors herein have discovered that creatine may be uniformly and accurately dispensed when completely dissolved in liquid. More specifically, the creatine has been created in the form of an effervescent in tablet or granular powder form which reduces the pH of water to thereby increase the solubility of the creatine in the liquid.

Creatine monohydrate, as used in the prior art, has a neutral pH which does not readily dissolve in water or other neutral pH liquids. The use of an acidic edible salt form of creatine, having a pH of approximately 4–5, makes the creatine much more soluble in the liquid form. The increase in solubility gives a much more uniform absorption of the creatine after ingestion.

In addition, because the creatine is packaged in either tablet or powder form, a precise amount of the compound is dissolved in the liquid, and ingested. The powder form used in the prior art required the consumer to scoop out predetermined amounts of the product and dissolve the product in water. The measuring process is typically inaccurate at the consumer level, since the typical consumer will not use precise measuring instruments to create the solution.

Because prior art formulations of creatine used creatine monohydrate in a neutral pH liquid, it was common to find undissolved creatine in the bottom of a glass, after the initial dose was ingested. To obtain the full effect of the dosage of creatine, it was then necessary to add more water to the remaining creatine in the bottom of the glass, stir the liquid to dissolve the remaining creatine, and then drink the second portion of liquid. Thus non-uniform dosages, and ingestion at non-uniform rates, are common in the prior art.

The use of an effervescent tablet, or packet of premeasured effervescent powder, assures complete and uniform dispersal of the creatine in the water, by virtue of the lowering of the pH of the liquid, and the effervescence of the liquid. The soluble effervescent will contain mixtures of acids (including but not limited to citric acid and/or tartaric acid) and sodium bicarbonate, which releases carbon dioxide when dissolved in water.

The chemical formula of creatine is C4 H9 N3 O2, and has a molecular weight 131.13. Prior art powder forms of creatine utilize creatine monohydrate in water, having a chemical formula of C4 H9 N3 O2 H2O. Creatine monohydrate becomes anhydrous at 100° F., and has a neutral reaction to litmus. One gram of creatine monohydrate dissolves in 75 ml of water, about 9 liters of alcohol, and is insoluble in ether. When creatine monohydrate is dissolved in an aqueous solution, creatinine is formed. While aqueous and alkaline solutions contain an equilibrium mixture of creatine and creatinine, it has been found that in an acid solution, the formation of creatinine is complete.

The method of the present invention relies upon the combination of creatine within an effervescent to create an acid solution which is ingested by the consumer. The effervescent lowers the pH to form an acid solution, whereby the creatine will completely and uniformly dissolve. Thus, in its most general form, the invention includes a soluble effervescent containing creatine, an acid, or mixture of acids, and a bicarbonate for releasing carbon dioxide when dissolved in a neutral pH liquid, such as water. In the preferred form of the invention, creatine citrate is utilized, while other acidic edible salt forms of creatine may be utilized, including creatine phosphate (C4 H10 N3 O5P, which may include either a sodium salt or a calcium salt) or creatine monohydrate.

The effervescent ingredients preferably utilize a mixture of acids, including citric acid and/or tartaric acid. Either sodium bicarbonate or potassium bicarbonate may be utilized for the release of carbon dioxide. In addition, starch (cellulose, alginic acid or other disintegrating agents), stearic acid (or other lubricants for tablet compression), and flavoring agents (either natural or synthetic) are utilized in the effervescent tablet.

While the effervescent is preferably in the form of a tablet, it may also be utilized in granular/powder form. The effervescent must be stored in a tightly closed container or other moisture-proof package, since water or other liquids will activate the effervescent. This is beneficial, because it permits a predetermined, premeasured amount of creatine and effervescent to be meted out within a package. In this way, the consumer will always receive the exact dosage of creatine desired, whether in tablet form or granular/powder form.

One form of creatine which has been found to accomplish the objectives of the present invention is manufactured in a 2.5 g tablet with creatine citrate, with the following composition:

| | |
|---|---|
| sodium carbonate | 50.0 mg |
| sodium bicarbonate | 1000.0 mg |
| citric acid | 1200.0 mg |
| dextrose | 1000.0 mg |
| creatine citrate | 2500.0 mg |
| sodium laurel sulfate | 5.0 mg |
| stevia (herbal sweetener) | 25.0 mg |
| magnesium stearate | 10.0 mg |
| natural orange flavor | 125.0 mg |

The amounts of bicarbonate and carbonate may vary by as much as 10%, with a corresponding inversely proportional variation of citric acid and the dextrose is used to compensate for tabletability. In addition, there may be a need to include polyethylene glycol in an amount up to 150 mg.

Effervescents are not to be swallowed directly, since they release carbon dioxide as they dissolve. Thus, the initial step in the method of the invention is to open a moisture-proof package containing the effervescent creatine, and dispense it into a glass of water or other pH neutral liquid. Once the effervescent creatine has completely dissolved, the solution should be swallowed immediately. As noted above, an acidic aqueous solution will eventually cause the creatine to completely convert to creatinine. While this conversion typically takes a number of hours, the longer the consumer waits to ingest the solution, the smaller the amount of beneficial creatine (and the greater the amount of undesirable creatinine) that will be present in the solution. Preferably, the solution is ingested within 15 minutes of being completely dissolved in the liquid.

Whereas the invention has been shown and described in connection with the preferred embodiment thereof, many modifications, substitutions and additions may be made which are within the intended broad scope of the appended claims.

I claim:

1. A method of enhancing delivery and uniformity of concentration of creatine in a human comprising the steps of:

dispensing a combination of an effervescent and a predetermined amount of creatine, into a neutral pH liquid;

dissolving the combination completely in the liquid to form an acid solution; and a human ingesting the solution.

2. The method of claim 1, wherein the dispensing step includes the initial step of opening a moisture-proof package containing the effervescent/creatine combination.

3. The method of claim 2, wherein the effervescent/creatine combination is in the form of a tablet.

4. The method of claim 2, wherein the effervescent/creatine combination is in the form of a powder.

5. The method of claim 1, wherein the dispensing step includes dispensing an effervescent tablet containing creatine citrate, and wherein the dissolving step includes dissolving the tablet in water.

6. The method of claim 1, wherein the dispensing step includes dispensing a premeasured amount of effervescent powder containing creatine citrate, and wherein the dissolving step includes dissolving the powder in water.

7. The method of claim 1, wherein the ingesting step is performed immediately after the combination is completely dissolved.

8. The method of claim 1, wherein the ingesting step is performed within approximately 15 minutes after the combination is completely dissolved.

9. In combination:

an effervescent; and creatine mixed with the effervescent in an amount which is effective to enhance a stable concentration of cellular creatine when dissolved in a neutral pH liquid and ingested by a human.

10. The combination of claim 9, wherein the effervescent is in the form of a tablet.

11. The combination of claim 9, wherein the effervescent is in the form of a powder.

12. The effervescent tablet of claim 3, wherein said creatine is in the form of an edible salt.

13. The combination of claim 9, wherein said effervescent includes an acid and a bicarbonate.

14. The combination tablet of claim 13, wherein the acid is selected from the group consisting of citric acid and tartaric acid.

15. The combination of claim 13, wherein the bicarbonate is selected from the group consisting of sodium bicarbonate and potassium bicarbonate.

16. The combination of claim 12, wherein said creatine is in the form of an acidic edible salt.

17. The combination of claim 16, wherein the creatine is selected from the group consisting of creatine monohydrate, creatine phosphate and creatine citrate.

18. The combination of claim 9, comprising an effervescent tablet including:

sodium carbonate 45–55 mg;

sodium bicarbonate 900–1100 mg;

citric acid 1080–1320 mg;

dextrose 900–1100 mg;

creative citrate 2500 mg;

sodium laurel sulfate 5 mg;

stevia 25 mg;

magnesium stearate 10 mg;

natural orange flavor 125 mg;

polyethylene glycol 0–150 mg.

19. The combination of claim 18, wherein the amount of sodium carbonate is 50 mg, the amount of sodium bicarbonate is 1 g, the amount of citric acid is 1.2 g and the amount of dextrose is 1 g.

* * * * *